(12) United States Patent
Jones

(10) Patent No.: US 7,771,990 B2
(45) Date of Patent: Aug. 10, 2010

(54) BIOLUMINESCENCE MONITOR

(75) Inventor: Gethin Rhys Jones, Bridgend (GB)

(73) Assignee: 3M Innovative Properties Company, St. Paul, MN (US)

( * ) Notice: Subject to any disclaimer, the term of this patent is extended or adjusted under 35 U.S.C. 154(b) by 615 days.

(21) Appl. No.: 10/966,203

(22) Filed: Oct. 15, 2004

(65) Prior Publication Data
US 2005/0089995 A1    Apr. 28, 2005

(30) Foreign Application Priority Data
Oct. 24, 2003    (GB) ................................ 0324784.8

(51) Int. Cl.
C12M 1/34    (2006.01)
C12M 3/00    (2006.01)
G01N 21/00    (2006.01)

(52) U.S. Cl. ................................. 435/288.7; 422/82.05
(58) Field of Classification Search .............. 435/288.7; 422/82.05
See application file for complete search history.

(56) References Cited

U.S. PATENT DOCUMENTS

| | | | |
|---|---|---|---|
| 4,717,545 A | 1/1988 | Morris | 422/56 |
| 4,772,561 A | 9/1988 | Genshaw | 436/169 |
| 4,839,295 A | 6/1989 | Smith | 436/86 |
| 4,916,060 A | 4/1990 | Weaver | 435/29 |
| 4,963,731 A * | 10/1990 | King | 250/559.2 |
| 5,307,146 A | 4/1994 | Porter et al. | 356/320 |
| 5,468,606 A | 11/1995 | Bogart et al. | 435/5 |
| 5,643,535 A * | 7/1997 | Smethers et al. | 422/82.05 |
| 5,922,609 A | 7/1999 | Kellner et al. | 436/103 |
| 6,136,611 A | 10/2000 | Saaski et al. | 436/527 |
| 6,317,207 B2 * | 11/2001 | French et al. | 356/317 |
| 6,466,316 B2 * | 10/2002 | Modlin et al. | 356/318 |
| 6,483,582 B2 * | 11/2002 | Modlin et al. | 356/317 |
| 6,982,431 B2 * | 1/2006 | Modlin et al. | 250/573 |

FOREIGN PATENT DOCUMENTS

| | | |
|---|---|---|
| GB | 2027193 | 2/1980 |
| GB | 2407638 | 5/2005 |
| WO | WO 89/07254 | 8/1989 |
| WO | WO 90/04775 * | 5/1990 |
| WO | WO2005/015610 | 2/2005 |
| WO | WO2006/004763 | 1/2006 |

* cited by examiner

Primary Examiner—Walter D Griffin
Assistant Examiner—Lydia Edwards
(74) Attorney, Agent, or Firm—Nancy M. Lambert

(57) ABSTRACT

A bioluminescence monitor comprises a photodetector 19 for detecting the amount of light emitted by a sample vessel 11 in a chamber 13. A reflector in the chamber 13 comprises a pair of elongate concave surfaces 16A, 16B which reflect a large proportion of the emitted light towards the photodetector 19. The monitor is calibrated by an LED 20 directed at the photodetector 19 and driven by a pulsed drive signal to provide a light output similar to the light output of an actual sample. The LED 20 is not continuously driven over the calibration period and thus does not heat up significantly enough to effect the level of the light output.

22 Claims, 2 Drawing Sheets

BIOLUMINESCENCE MONITOR

BACKGROUND OF THE INVENTION

1. Field of the Invention

This invention relates to an instrument for monitoring light emission, particularly but not solely used in hygiene or biomass monitoring using the adenosine triphosphate dependent bioluminescent firefly luciferin/luciferase reaction.

2. Related Background Art

Luminometers for detecting the emission of light from a test sample are widely used to measure chemical and biological parameters in various types of samples by use of reagents which give rise to light through bioluminescent or chemiluminescent based reactions.

It is known to test for bacteria or other living cells by taking a sample and releasing adenosine triphosphate (ATP) contained within the cells using an appropriate reagent. Being a chemical compound common to all living cells, ATP is found in almost all foodstuffs of biological origin, within intact cells or as extracellular ATP. The level of ATP in a sample of a surface or rinse water may therefore be used as an indication of hygiene after cleaning, indicating the level of residues of food and/or microorganisms. The level of ATP can also be used in process and waste water, water tanks and cooling towers as a measure of biomass to follow the effect of biocide treatment. Many other applications of ATP bioluminescence are known conditions.

Bioluminescence monitors are well known. One such monitor is disclosed in WO90/04775 and comprises a chamber into which a elongate vessel containing the reagents can be inserted. A light detector, such as a photomultiplier tube or photodiode is disposed at the bottom of the chamber for measuring the amount of light which is emitted from the sample. The output of the light detector is connected to an electronic circuit which converts the measured light output to provide an indication of hygiene.

It will be appreciated that the monitor needs to be calibrated so that a correct indication of hygiene is provided according to the level of light which is output from the sample. Initially, this is performed in the factory where the monitor is produced using a sample which is inserted into an accurately calibrated test instrument and comparing the reading against the reading taken from the instrument under test using the same test sample. The monitor under test can then be adjusted to provide the same output as the calibrated test instrument.

It will be appreciated that it is desirable to check the calibration of the monitor on a regular basis. Hitherto this has been achieved by returning the monitor to a calibration center where the above-mentioned calibration procedure can be repeated.

In order to avoid the inconvenience of having to return the monitor to a calibration center, it has been proposed to provide users with a calibration checking device which emits a known amount of light. This device can be inserted into the monitor to check that the monitor measures the correct level of light.

A disadvantage of this is that the calibration checking device comprises plastics scintillant and a radio active light emitting material, such as carbon 14, which is potentially hazardous to the user. Also, the level of the light output of the calibration device falls as the scintillant material decays over time and thus an inaccurate calibration reading is provided. Another disadvantage is that the wavelength of the light output by the scintillant is substantially different from that of an actual sample.

It is also known to provide a monitor having a built-in calibration device comprising a light emitting diode (LED) or other light source directed at the photodetector. Whilst the wavelength of the light output by an LED is closer to that of an actual sample, the light output by an actual sample is very low, and the monitor has to be calibrated at this low level where even individual photons can be detected. Thus, the output of the LED has be to substantially attenuated, for example by placing a large block of semi-opaque plastics material between the LED and the photodetector.

Generally, calibration is performed by taking a reading over a period of 10 seconds or so. A disadvantage of this is that the output of the LED varies as it heats up over the calibration period, with the result that inaccuracies occur.

An other disadvantage of using an LED is that the light emitted is continuous, unlike the output of an actual test sample in which photons are randomly emitted.

SUMMARY OF THE INVENTION

We have now devised a bioluminescence monitor which alleviates the above-mentioned problems.

In accordance with this invention as seen from a first aspect, there is provided a bioluminescence monitor comprising a sample chamber for receiving a vessel containing a light-emitting substance, a photodetector for receiving the emitted light and connected to an electronic circuit for measuring the light received by the photodetector, and calibration means comprising a light emitting diode arrangeable to direct light at the photodetector, the light emitting diode being connected to a drive circuit which applies a pulsed drive signal to the light emitting diode.

The use of a pulsed drive signal means that the light emitting diode is not continuously driven over the calibration period and thus does not heat up significantly enough to effect the level of the light output.

Also, the pulsed nature of the light output is similar to the output of the actual sample. Accordingly, calibration is performed in close to realistic light conditions.

Preferably the drive circuit is arranged to drive the light emitting diode with pulses having a period of 1 to 40 ns. Pulses of this short duration have a similar period to the pulses of light produced by an actual test sample.

The drive circuit maybe arranged to drive the light emitting diode with successive individual pulses or bursts of pulses, the period between successive individual pulses or bursts being long compared with the period of the pulses.

In one embodiment, the light emitting diode is preferably mounted in a device which can be inserted into the chamber instead of the vessel.

In order to exclude light from the chamber during tests, a closure is provided on the sample chamber which can be closed once the vessel has been inserted. Preferably the device is battery powered, a switch preferably being provided on the device for actuating the light emitting diode when the closure is closed.

In an alternative embodiment, the light emitting diode is permanently mounted in the monitor.

Preferably a reflector is provided in the chamber, the reflector having a front surface arranged to reflect light from the sample towards the photodetector, the light emitting diode being mounted behind the reflector to emit light through the reflector towards the photodetector.

Preferably, the light emitting diode emits light towards the photodetector through an aperture in the reflector.

As mentioned hereinbefore, the amount of light emitted by the sample is very low and thus it is desirable to direct as much of the generated light as possible towards the photodetector.

Thus in accordance with this invention as seen from a second aspect, there is provided a monitor for use in sample testing, comprising an elongate sample chamber for receiving an elongate tubular vessel containing a light emitting substance, a photodetector for receiving the emitted light and connected to an electrical circuit for measuring the light received by the photodetector, and a reflector arranged to reflect emitted light radiating away from the photodetector theretowards, the reflector comprising a pair of elongate reflective surfaces extending longitudinally of sample chamber, each surface being concave in section and being directed towards the photodetector.

The provision of two concave reflective surfaces directs light radiating away from the sample vessel towards the photodetector in such a manner that the sample vessel does not interfere with the path of the reflected light. In this manner, a large proportion of the light emitted by the sample is directed towards the photodetector.

Preferably the photodetector is disposed on one side of the sample chamber, on a line which extends radially of the chamber, the reflector being disposed on the opposite side of the chamber with the elongate reflective surfaces preferably being directed along respective lines which converge towards the photodetector.

Preferably the photodetector is directed along a line which extends parallel to the longitudinal axis of the sample chamber, a further reflective surface being disposed in front of the photodetector to reflect light emitted radially from the sample and from said reflective surfaces into the photodetector.

Preferably the pair of elongate concave reflective surfaces are directed at said further reflective surface, which then directs the light into the photodetector.

Preferably said further reflective surface lies in the plane which extends at an inclined angle to the directional axis of the photodetector and at an inclined angle to a line which extends radially outwards of the sample vessel at 90° to the longitudinal axis thereof.

Preferably said further reflective surface is concave.

Preferably the pair of elongate concave reflective surfaces are positioned side-by-side and curve in respective opposite directions from a line which extends parallel to the axis of the chamber adjacent said vessel.

Preferably the reflective surfaces are provided on a one-piece reflective member positioned inside the chamber.

Preferably the one-piece reflective member forms an enclosure having top, bottom and side walls, the reflective surfaces being provided on the side walls of the enclosure.

Preferably the internal surfaces of each of the walls are reflective.

BRIEF DESCRIPTION OF THE DRAWINGS

An embodiment of this invention will now be described by way of an example only and with reference to the accompanying drawings, in which.

DETAILED DESCRIPTION OF THE PREFERRED EMBODIMENTS

Figure 1:
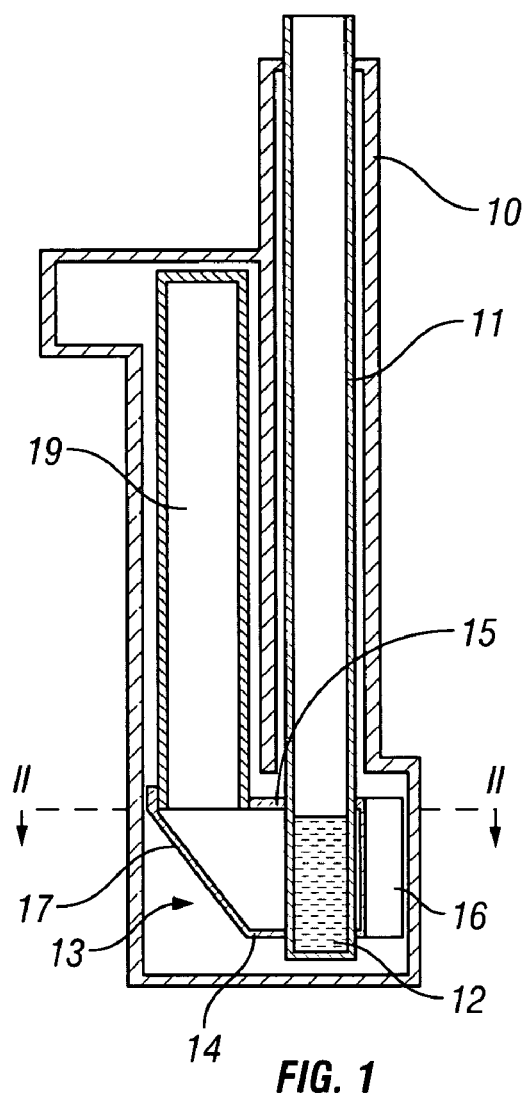
FIG. 1 is a longitudinal section through a sampling portion of a bioluminescence hygiene monitor in accordance with this invention.
Figure 2:
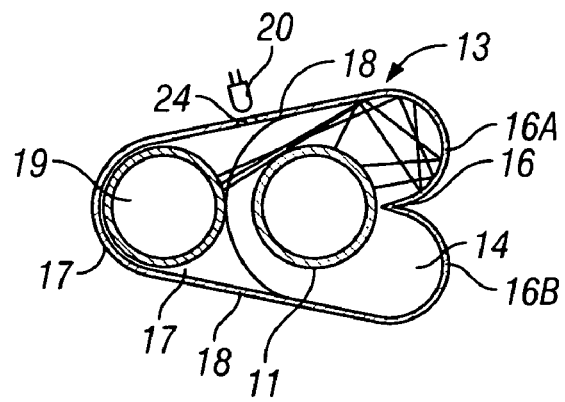
FIG. 2 is a sectional view along the line II-II of FIG. 1.

Referring to FIGS. 1 and 2 of the drawings, bioluminescence hygiene monitor comprises a housing (not shown) having an upwardly facing aperture which communicates with a elongate sample chamber 10 for receiving an elongate sample vessel 11 containing a reagent 12.

A sensing chamber 13 is disposed at the base of the sample chamber 10 and comprises a bottom wall 14, a top wall 15, first and second end walls 16, 17 and opposite side walls 18. The bottom end and side walls 14, 16, 17, 18 are formed as a one-piece body of plastics material by injection molding, the top wall is formed separately to facilitate molding and is snap engaged onto the body during assembly of the monitor.

The top wall 15 of the sensing chamber 13 is provided with an aperture disposed at a point intermediate the opposite side walls 18 and adjacent the first end wall 16. The aperture in the top wall 15 is aligned with the upper end of the sample chamber 10, so that the lower end of a sample vessel 11 extends into the sensing chamber 13 when the monitor is in use.

An elongate photomultiplier tube 19 extends parallel to the upper elongate portion of the sample chamber 10, the lower sensing end of the photomultiplier tube 15 extending partially into the sensing chamber 13 through an aperture formed in the top wall 15 adjacent to the second end wall 17 of the chamber 13.

The first end wall 16 comprises two arcuate portions 16A, 16B which curve outwardly in respective opposite directions from a point disposed intermediate the side walls 18 and which then curve inwardly and meet the respective side walls 18, thereby defining respective concave surfaces directed towards the second end wall 17 of the chamber 13.

The second end wall 17 of the chamber 13 extends outwardly and upwardly from the bottom wall 14 of the chamber, substantially in a plane which lies at 45° to the longitudinal axis of the photomultiplier tube 19. The inclined second end wall 17 is also concave. The photomultiplier tube 19 is directed downwardly at the internal surface of the inclined second end wall 17.

All of the internal surfaces of the sensing chamber 13 are coated with a highly reflective material. The external surfaces of chamber 13 may also be coated with the same highly reflective material.

In use, light can radiate from the vessel 11 in any radial direction. Some of the radiated light falls directly on the inclined second end wall 17 and is reflected into the photomultiplier tube 19. Any light which is radiated towards the first end wall 16 of the chamber 13 is reflected by the concave surfaces provided by the arcuate portions 16A, 16B onto a side wall 18 and then towards the inclined second end wall 17 and into the photomultiplier tube 19. The shape of the end wall 16 is such that a large percentage of the emitted light radiating away from the photomultiplier tube 19 is reflected back towards the photomultiplier tube 19 in such a manner that it does not collide with the vessel 11.

Accordingly, it will be appreciated that a high proportion of the photons emitted from the sample vessel 11 will be collected by the photomultiplier tube 19.

As shown in FIG. 2 of the drawings, a light emitting diode 20 is mounted adjacent a side wall 18 of the sensing chamber 13 and is arranged to direct light through an aperture 24 in the wall of the chamber 13 towards the photomultiplier tube 19.

Figure 3:
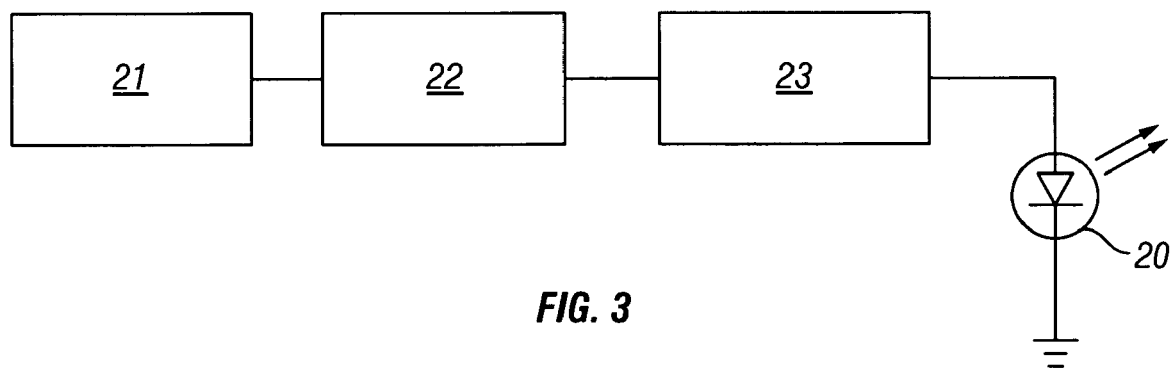
FIG. 3 is a schematic diagram of a circuit of the monitor of FIG. 1 for producing a calibration signal.

Referring to FIG. 3 of the drawings, the LED 20 is connected to a drive circuit comprising a microprocessor 21 which controls a programmable pulse generator 22. The output of the pulse generator 22 is connected to the LED 20 via a pulse shaper circuit 23.

Figure 4:
FIGS. 4 and 5 are waveform diagrams of alternative calibration signals.
Figure 5:

Referring to FIGS. 4 and 5 of the drawings, the programmable pulse generator 22 is controlled by the microprocessor 21 to produce an output comprising successive pulses or groups of pulses. The period of each pulse or group pulses can be controlled by the microprocessor 21, which can also control the width of the pulses as well as the period of the pulses in each group and the number of pulses in each group. Once the microprocessor 21 has been configured, the programmable pulse generator 22 produces successive pulses or groups of pulses with the chosen parameters. We have found that a single pulse having a period of 1 to 4 ns produces a low but measurable output from the LED 20.

Following manufacture of a monitor, it is initially calibrated by inserting a sample into an accurately calibrated test instrument and taking a reading of the light output. The same test sample is then inserted into the monitor to be calibrated and the reading taken from the monitor is then compared against that of the accurately calibrated test instrument. The monitor being tested is then adjusted so that the same reading as the accurately calibrated is provided.

The instrument being calibrated is then switched into its calibration mode, wherein a pulsed signal is applied to the LED 20. A reading of the light level is then taken and stored in a memory device inside the monitor.

A user is able to regularly check the calibration of the monitor which they are using by switching the monitor into its calibration mode, wherein the LED 20 is again illuminated over a period of 10 seconds or so and a reading taken. This reading is then compared with the reading stored in memory and an indication that the monitor is out of calibration can be provided if the measured reading is different from the stored reading by more than a predetermined amount. In this event, the user can return their monitor for re-calibration.

In an alternative embodiment, the software inside the monitor can use the difference between the measured and stored readings to automatically re-calibrate the monitor.

While the preferred embodiment of the invention has been shown and described, it will be understood by those skilled in the art that changes of modifications may be made thereto without departing from the true spirit and scope of the invention.

I claim:

1. A bioluminescence monitor comprising
   a sample chamber for receiving a vessel containing a light-emitting substance,
   a photodetector for receiving the emitted light,
   an electronic circuit connected to the photodetector, wherein the electronic circuit measures the light received by the photodetector,
   calibration means comprising a light emitting diode that directs light at the photodetector and a drive circuit connected to the light emitting diode, wherein the drive circuit applies a pulsed drive signal to the light emitting diode.

2. A bioluminescence monitor as claimed in claim 1, in which the drive circuit drives the light emitting diode with pulses having a period of between 1 and 40 ns.

3. A bioluminescence monitor as claimed in claim 1, in which the drive circuit drives the light emitting diode with successive individual pulses, wherein the period between successive individual pulses is longer than the period of the pulses.

4. A bioluminescence monitor as claimed in claim 1, in which the drive circuit drives the light emitting diode with successive bursts of pulses, wherein the period between successive bursts of pulses is longer than the period of the pulses.

5. A bioluminescence monitor as claimed in claim 1, in which the light emitting diode is mounted in a device which is removably mounted in said chamber.

6. A bioluminescence monitor as claimed in claim 5, in which a closure is provided on said chamber which can be closed once the vessel has been inserted.

7. A bioluminescence monitor as claimed in claim 6, wherein the device is battery powered, and wherein the device comprises a switch for actuating the light emitting diode when the closure is closed.

8. A bioluminescence monitor as claimed in claim 1, in which the light emitting diode is permanently mounted in the chamber.

9. A bioluminescence monitor as claimed in claim 8, in which a reflector is provided in the chamber, the reflector having a front surface arranged to reflect light from the sample towards the photodetector, the light emitting diode being mounted behind the reflector to emit light through the reflector towards the photodetector.

10. A bioluminescence monitor as claimed in claim 9, in which the light emitting diode emits light towards the photodetector through an aperture in the reflector.

11. The bioluminescence monitor of claim 1, further comprising a reflector that reflects emitted light radiating away from the photodetector theretowards.

12. A bioluminescence monitor according to claim 11, wherein the reflector comprises a pair of elongate reflective surfaces extending longitudinally of sample chamber, each surface being concave in section and being directed towards the photodetector.

13. A bioluminescence monitor according to claim 11, in which said light emitting diode emits light towards the photodetector through an aperture in the reflector.

14. A bioluminescence monitor as claimed in claim 11, in which the photodetector is disposed on one side of the sample chamber, on a line which extends radially of the chamber, the reflector being disposed on the opposite side of the chamber with the elongate reflective surfaces being directed along respective lines which converge towards the photodetector.

15. A bioluminescence monitor as claimed in claim 11, in which the photodetector is directed along a line which extends parallel to the longitudinal axis of the sample chamber, a further reflective surface being disposed in front of the photodetector to reflect light emitted radially from the sample and from said reflective surfaces into the photodetector.

16. A bioluminescence monitor as claimed in claim 15, in which the pair of elongate concave reflective surfaces are directed at said further reflective surface.

17. A bioluminescence monitor as claimed in claim 15, in which said further reflective surface lies in the plane which extends at an inclined angle to the directional axis of the photodetector and at an inclined angle to a line which extends radially outwards of the sample vessel at 90 degrees to the longitudinal axis thereof 18. A bioluminescence monitor as claimed in claim 15, in which said further reflective surface is concave.

19. A bioluminescence monitor as claimed in claim 12, in which the pair of elongate concave reflective surfaces are positioned side-by-side and curve in respective opposite directions from a line which extends parallel to the axis of the chamber adjacent said vessel.

20. A bioluminescence monitor as claimed in claim 12, in which the reflective surfaces are provided on a one-piece reflective member positioned inside the chamber.

21. A bioluminescence monitor as claimed in claim 20, in which the one-piece reflective member forms an enclosure having top, bottom and side walls, the reflective surfaces being provided on the side walls of the enclosure.

22. A bioluminescence monitor as claimed in claim 20, in which the internal surfaces of each of the walls of the chamber are reflective.

* * * * *